(12) United States Patent
Pierry

(10) Patent No.: US 7,556,039 B1
(45) Date of Patent: Jul. 7, 2009

(54) SIDESTREAM GAS SAMPLING SYSTEM USING A CAPILLARY TUBE FLOW SENSOR

(75) Inventor: Anthony T Pierry, Plantsville, CT (US)

(73) Assignee: Ric Investments, Inc., Wilmington, DE (US)

( * ) Notice: Subject to any disclaimer, the term of this patent is extended or adjusted under 35 U.S.C. 154(b) by 810 days.

(21) Appl. No.: 10/782,216

(22) Filed: Feb. 19, 2004

(51) Int. Cl.
*A61M 16/00* (2006.01)
(52) U.S. Cl. .......................... 128/204.22; 128/204.21; 128/204.18
(58) Field of Classification Search ............ 128/201.25, 128/202.16, 203.24, 204.22, 204.21, 205.21, 128/204.18; 600/529–533, 538, 476, 477; 73/23.2, 23.3, 23.35–23.37, 23.41, 861.43, 73/861.69
See application file for complete search history.

(56) References Cited

U.S. PATENT DOCUMENTS

| | | | |
|---|---|---|---|
| 4,177,381 A | 12/1979 | McClatchie et al. | |
| 4,228,352 A * | 10/1980 | Adrian | 250/343 |
| 4,692,621 A | 9/1987 | Passaro et al. | |
| 4,914,720 A | 4/1990 | Knodle et al. | |
| 4,958,075 A * | 9/1990 | Mace et al. | 250/343 |
| 5,245,859 A * | 9/1993 | Smith et al. | 73/38 |
| 5,282,473 A | 2/1994 | Braig et al. | |
| 5,379,650 A * | 1/1995 | Kofoed et al. | 73/861.52 |
| 5,932,877 A | 8/1999 | Braig et al. | |
| 6,305,212 B1 * | 10/2001 | Drzewiecki | 73/23.2 |
| 6,813,929 B2 * | 11/2004 | Jochum, Jr. | 73/23.27 |

\* cited by examiner

*Primary Examiner*—Danton DeMille

(57) ABSTRACT

A sidestream gas sampling system that includes a conduit that communicates a flow of gas to a gas measurement site. A gas measurement assembly measures a constituent of the flow of gas at the gas measurement site. A capillary tube communicates the flow of gas from the gas measurement site. A differential pressure transducer in fluid communication with first and second portions of the capillary tube measure a pressure differential between these two portions. A controller is coupled to the differential pressure transducer to measure the flow of gas based on the output of the differential pressure transducer and to control the flow of gas via a flow generator coupled to the gas flow path.

20 Claims, 3 Drawing Sheets

SIDESTREAM GAS SAMPLING SYSTEM USING A CAPILLARY TUBE FLOW SENSOR

BACKGROUND OF THE INVENTION

1. Field of the Invention

The present invention relates to a sidestream respiratory gas sampling system with flow based feedback control, and, in particular, such a sidestream sampling system that utilizes a pressure drop across a capillary tube to measure and control the sidestream flow.

2. Description of the Related Art

Gas analyzers are widely used in medical applications and are typically categorized into two different types: (1) "diverting" or "sidestream" gas sampling systems; and (2) "non-diverting" or "mainstream" gas sampling systems. A mainstream gas sampling system includes a sample cell that is disposed along the main path of a breathing circuit through which a patient's respiratory gases flow. As a result, the patient's inspired and expired respiratory gases pass through a sample cell, which is also known as a "cuvette". A gas measurement system, which includes the elements necessary for monitoring respiratory gases, such as a radiation source and detector, is coupled to the sample cell to measure the constituents of gas passing through the sample cell. An example of such a conventional mainstream gas measurement system is shown in U.S. Pat. No. 4,914,720 to Knodle et al.

A sidestream type of gas sampling system transports a portion of sampled gases from the sampling site, which is typically a breathing circuit coupled to the patient's airway or directly at the patient's airway, through a sampling tube to the sample cell, where the constituents of the gas are measured by a gas sensing system. Gases are continuously aspirated from the sample site, through the sampling tube, and into the sample cell, which is located within a gas measurement instrument. To obtain good quality capnographic waveforms and accurate $CO_2$ measurements, the gas stream flow rate must be well regulated using a flow controller, such as a closed loop or feedback flow control system.

Flow control systems known in the art utilize an orifice to generate a pressure drop to measure the flow rate. The speed of a pump used to draw gas to the sample site is adjusted to maintain a constant gas stream flow rate through the sample site. The pressure drop across the orifice is affected by the density of the gas. As a result, the pressure drop that occurs across the orifice is altitude dependent and is affected significantly by the composition of the gas. The volumetric flow (Q) through an orifice is derived using Bernoulli's principle, and can be easily shown as:

$$Q = K\sqrt{\frac{2*\Delta P}{\rho}}, \quad (1)$$

where K is a constant derived from the orifice dimensions, $\Delta P$ is the pressure drop across the orifice, and $\rho$ is the density of the gas. It can thus be appreciated that the density of the gas plays a major role in volumetric flow measurements using an orifice.

Gas density is proportional to pressure, and atmospheric pressure is inversely proportional to altitude. Using an orifice to regulate flow can result in an increase in flow rate as gas density decreases, such as at increasing altitude, i.e., the pressure decreases. Similarly, gas density may change significantly from nominal conditions due to the administration of therapeutic gas mixtures, such as helium and oxygen, to the flow of gas being delivered to the patient. Gas stream flow rates in known sidestream systems range from about 50 ml/min to about 250 ml/min. Examples of conventional sidestream gas sampling systems are taught in U.S. Pat. Nos. 4,692,621 to Passaro et al.; 4,177,381 to McClatchie; 5,282,473 to Braig et al.; and 5,932,877 also issued to Braig et al.

Conventionally, the sampling ports used by sidestream gas sampling systems are located in a wall of the respiratory circuit or an airway adapter. The location of the sampling port along a breathing circuit may range anywhere from an elbow connected to an endotracheal tube, to a wye (Y) connector at the opposite end of a breathing circuit. For example, the sampling port may be placed on the ventilator side of an in-line filter or heat-moisture exchanger (HME). This results in a drier sampling tube but with the inherent risk of significant distortion of the capnographic waveform and lower end-tidal values.

It is also well known in the art to locate the sampling port on the patient side of the in-line filter. However, there is a possibility of an accumulation of condensate and/or patient secretions in this configuration for a sidestream sampling system. Condensation from a humidified sample gas, in combination with patient secretions, can block and contaminate the sampling tube, which may necessitate frequent replacement. The effectiveness of water traps and water filters vary between manufacturers, but no water trap or water filter is immune to eventual clogging and distortion of the capnographic waveform, particularly if preventive maintenance is inadequate. Additionally, water and/or contaminants may break through the filter, clogging the system at the point of smallest cross-sectional area, namely the orifice used for flow control.

Given these problems with sidestream capnography, it is desirable to provide a sidestream gas sampling flow control system that is (a) less affected by altitude and the composition of the gas, and (b) less likely to become occluded by condensate and/or patient secretions than conventional systems.

SUMMARY OF THE INVENTION

Accordingly, it is an object of the present invention to provide a sidestream gas sampling system that overcomes the shortcomings of conventional sidestream gas sampling systems. This object is achieved according to the principles of the present invention by providing a sidestream gas sampling system that includes a conduit adapted to communicate a flow of gas to a gas measurement site and a gas measurement assembly that measures a constituent of the flow of gas at the gas measurement site. A capillary tube communicates the flow of gas from the gas measurement site, and a differential pressure transducer is provided in fluid communication with a first portion and a second portion of the capillary tube. The first and second portions are spaced sufficiently far apart from one another such that a pressure differential exists therebetween. A controller measures the flow of gas based on the output of the differential pressure transducer and controls the flow of gas via a flow generator, such as a pump.

The pressure drop across the capillary tube is used to determine the flow of gas, in particular, the flow of gas through the gas measurement site. A capillary tube for flow control is not substantially affected by altitude and the composition of the gas. It is also less prone to clogging, thereby reducing the need for costly preventive maintenance required by conventional orifice based sidestream gas monitoring systems.

Existing sidestream $CO_2$ analyzers measure the pressure drop across an orifice to control the flow rate of the sampling system. The method of the invention measures the pressure drop across a capillary tube, which is not dependent on gas density, to control the sampling flow rate. The sidestream flow controller, according to the method of the invention, controls the sampling flow rate by measuring the pressure differential across a capillary tube. An advantage of this capillary-based flow control system is that it is only influenced by viscosity, which varies substantially less than density across the wide variety of gases, including anesthetic and therapeutic gases that may pass through the gas sampling system. Therefore the flow rate of the capillary tube based system of the present invention varies less with different gas constituents than a conventional orifice-based system. Another advantage of the capillary-based flow control system of the present invention is that the changes in density of the sample gas caused by changes in altitude or atmospheric pressure do not cause variations of the flow rate.

Yet another advantage of the capillary-based flow control system of the present invention is that it is less likely to clog relative to conventional orifice-based systems. The system of the present invention improves the reliability of the sidestream gas monitoring systems. The use of a removable sample cell, in conjunction with reduced risk of clogging of the capillary flow control system of the present invention, provides a robust sidestream $CO_2$ system that is impervious to the typical "maintenance" problems associated with conventional sidestream gas monitoring systems. Conventional sidestream systems clog easily and frustrate the user to the point of discouraging their use because "it is too much trouble."

These and other objects, features, and characteristics of the present invention, as well as the methods of operation and functions of the related elements of structure and the combination of parts and economies of manufacture, will become more apparent upon consideration of the following description and the appended claims with reference to the accompanying drawings, all of which form a part of this specification, wherein like reference numerals designate corresponding parts in the various figures. It is to be expressly understood, however, that the drawings are for the purpose of illustration and description only and are not intended as a definition of the limits of the invention. As used in the specification and in the claims, the singular form of "a", "an", and "the" include plural referents unless the context clearly dictates otherwise.

DETAILED DESCRIPTION OF THE PRESENTLY PREFERRED EMBODIMENTS OF THE INVENTION

Figure 1:
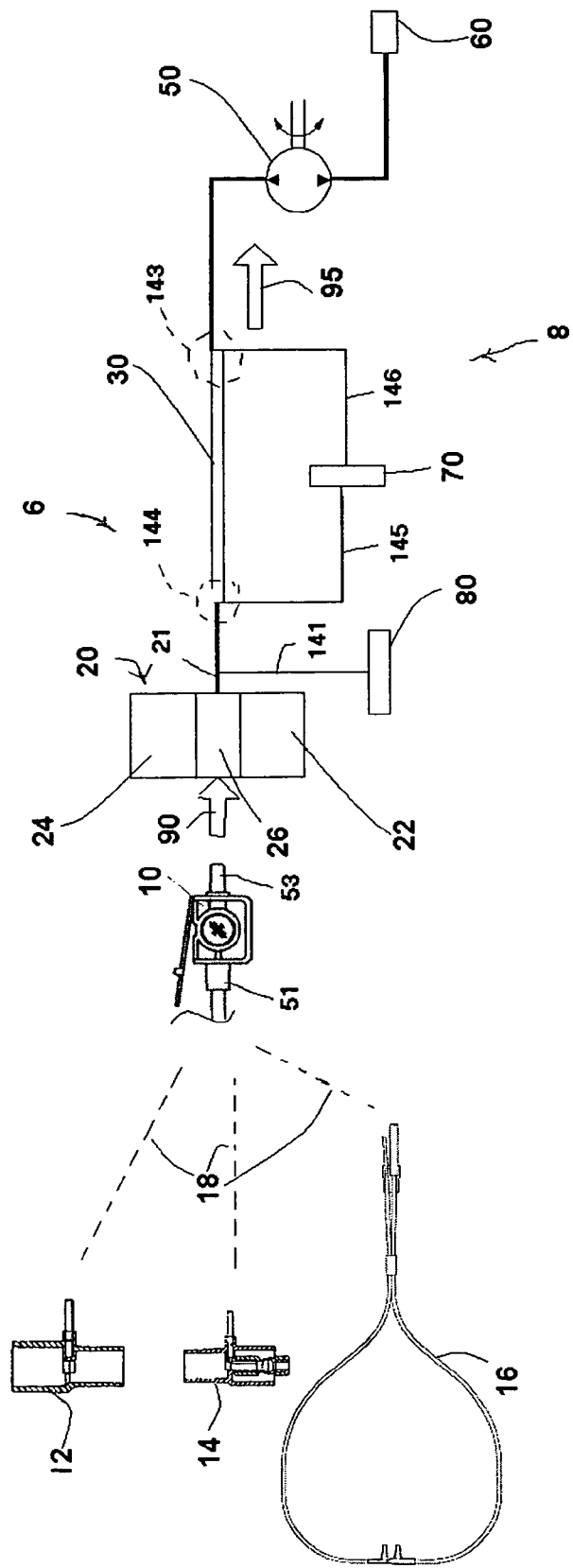
FIG. 1 is a schematic diagram of a sidestream gas sampling system according to the principles of the present invention, and illustrating examples of differing patient interface options suitable for use therewith.

FIG. 1 is a high-level schematic diagram of a sidestream gas sampling system 6 according to the principles of the present invention. Sidestream gas sampling system 6 includes a flow monitoring/control system 8, which is discussed in greater detail below, and a gas measurement system 20. FIG. 1 also illustrates a variety of different patient interface devices suitable for use with the sidestream gas sampling system.

Sidestream gas sampling is used on both intubated and non-intubated patients ranging from neonates to adults. To accommodate these different applications, different patient interface devices must be used. FIG. 1 illustrates one set of patient interface devices that can be coupled to a common removable sample cell 10 via a conduit, indicated schematically at 18. An exemplary configuration for a sample cell that is suitable for use in the present sidestream gas sampling system is the subject of pending U.S. application Ser. No. 10/384,329, entitled "Sidestream Gas Sampling System with Detachable Sample Cell", filed Mar. 3, 2003, ("the '329 application") the contents of which are incorporated herein by reference. Patient interface devices that accommodate the different applications for the sidestream gas sampling system include, but are not limited, to a pediatric/adult airway adapter 12, a neonatal airway adapter 14, or a nasal cannula 16. Adapters 12 and 14 are typically provided in-line in a breathing circuit, while nasal cannula 16 is worn by the patient so that gas exhaled through the patient's nose enters the prongs of the cannula.

Sample cell 10, which provides a gas measurement site at which the constituents of the gas are measured, inserts into a sample cell receptacle 26 of gas measurement assembly 20. Gas measurement assembly 26 includes an emitter 22 that emits radiant energy through the gas at the gas measurement site, and a detector 24 that receives the radiant energy passing through the gas at the gas measurement site. The output of the detector is used, as known in the art, to measure the constituents of the flow of gas, generally indicated by arrow 90, passing through the gas measurement site.

Gas flow 90 is drawn by a flow generator, such as a pump, 50 through conduit 18 into the sample cell via an inlet port 51. After exiting the sample cell via an exit port 53, the flow of gas passes through a T-fitting 21. A pressure sensing line 23 is connected to T-fitting 21 and to a pressure sensor 80. A capillary tube 30, which is a unique feature of the present invention, is also coupled to T-fitting 21. Pressure sensor 80 measures pressure near sample cell 10. In the illustrated exemplary embodiment, T-fittings 143 and 144 are connected to each end of capillary tube 30. Pressure sensing lines 145 and 146 are coupled to T-fittings 143 and 144 are to opposites portions of a differential pressure sensor 70. The flow of gas, as indicated by arrow 95, then passes through pump 50 prior to exiting the pneumatic circuit via an outlet port 60.

Figure 2:
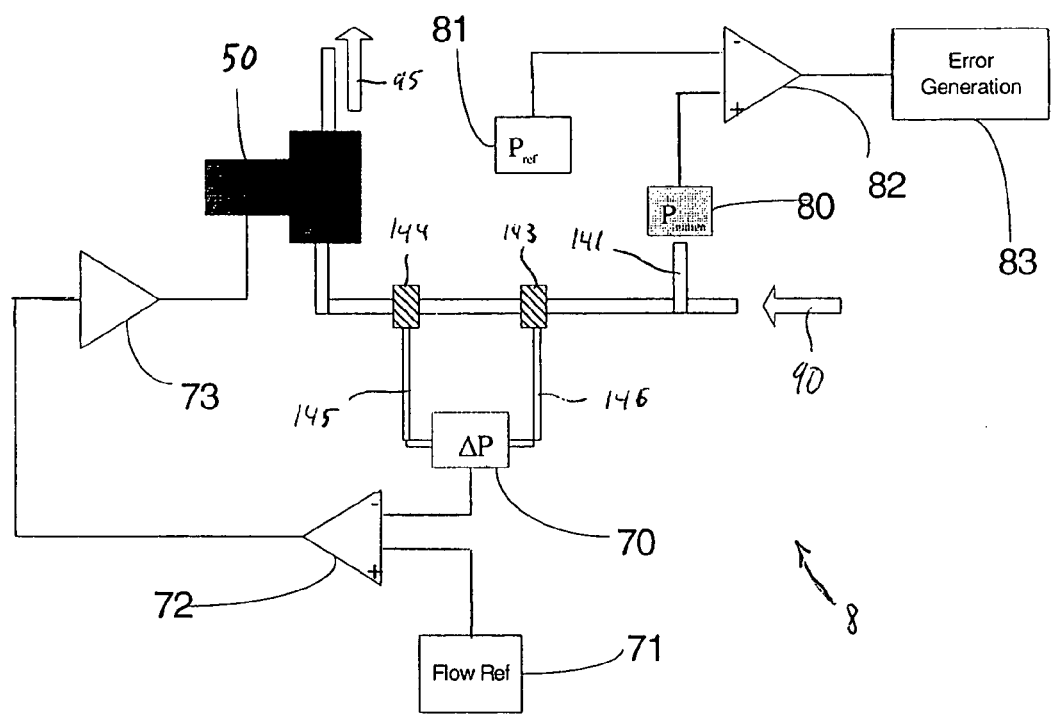
FIG. 2 is a schematic diagram of the flow monitoring/control system of the sidestream gas sampling system of FIG. 1.

FIG. 2 is schematic diagram showing flow monitoring/control system 8 in greater detail. Flow rate regulation is accomplished by closed loop control of flow generator 50 with feedback from differential pressure measured across a length of capillary tube 30 located on the inlet side of the flow generator. It is to be understood that the present invention contemplates locating the capillary tube at the outlet of the flow generator or anywhere between the patient interface and outlet of the gas sampling system.

The output signal from differential pressure transducer 70, which is in fluid communication with a first portion and a second portion of capillary tube 30, is related to flow through the relationship expressed by Poiseuille's Law. The difference between an output signal from the pressure transducer 70 and the signal from flow reference 71 is determined by a comparator 72. The output signal of comparator 72 serves as input to a driver 73, which controls the speed of flow generator 50. In a preferred embodiment of the present invention, this arrangement maintains a constant rate of flow for the gas through the capillary tube, and, hence, through the gas sampling site.

It is to be understood that this simple feedback system is only illustrative of one possible embodiment. Conventional feedback approaches such as proportional-integral-derivative (PID) control, as well as more sophisticated control methods, as known in the art, may be used. The feedback control may be a totally analog circuit, as illustrated, a digital/software based circuit, or a combination of the two approaches. Additionally, the present invention contemplates that flow generator 50 may be any device suitable for generating such flow. Of course, the flow generator used must be capable of being controlled by the control techniques of the present invention.

As noted above, pressure sensor 80 is used to measure the sample cell pressure. This is done to detect a pneumatic occlusion on the gas flow path. Additionally, the difference between a pressure reference 81 and the output signal from pressure transducer 80 is determined by a comparator 82. This difference serves as input to an error generation circuitry/software 83. For example, an occlusion caused by the presence of contaminants in the sampling path, including conduit 18, the T-fittings, or capillary tube 30, can be detected by a change in the flow as measured by differential pressure sensor 70. Also, a leak or disconnection along the gas flow path is detected by a change in pressure measured by pressure sensor 80.

Figure 3:
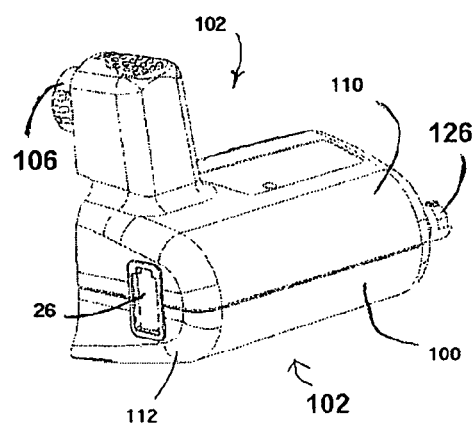
FIG. 3 is a perspective view of an exemplary embodiment of a housing containing the sidestream gas sampling system of the present invention and that is adapted to be coupled to a multi-parameter monitoring system.
Figure 4:
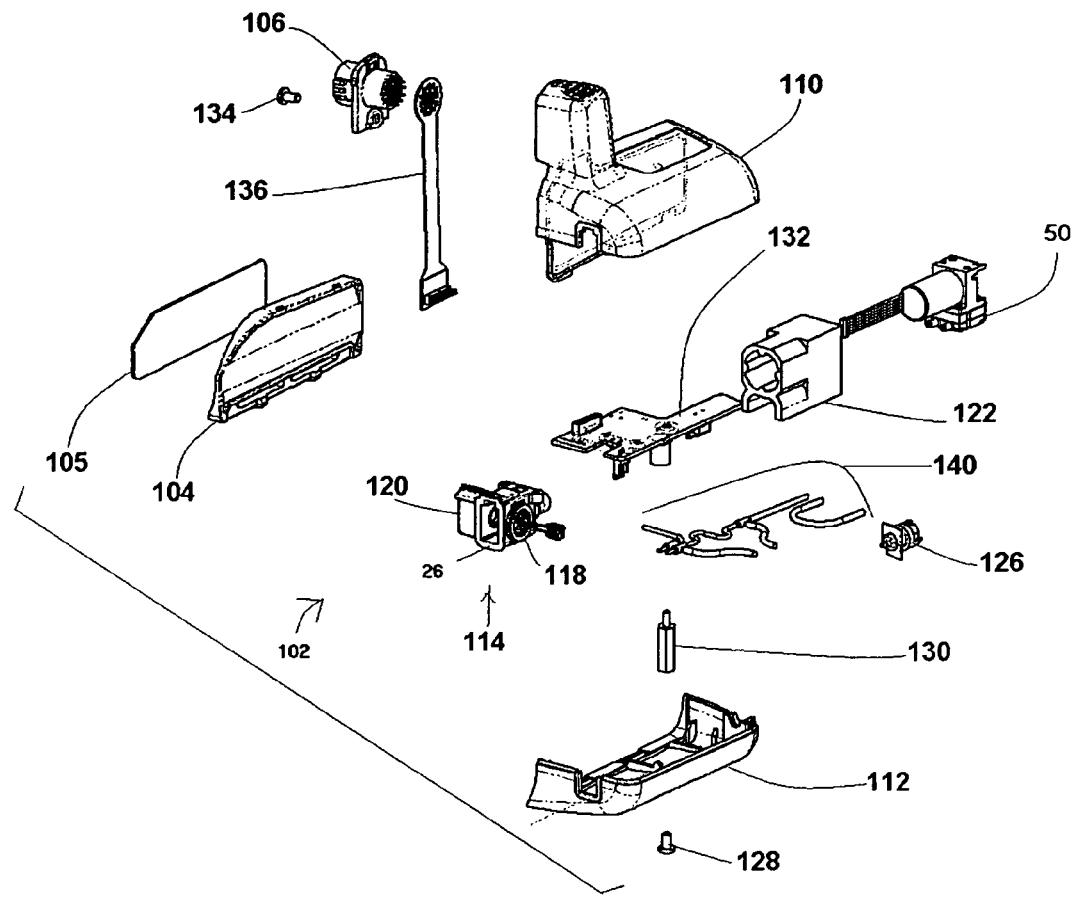
FIG. 4 is an exploded view of the housing of FIG. 3 and the sidestream gas measurement assembly contained therein, including the flow monitoring/control system corresponding to that shown in FIG. 2.
Figure 5:
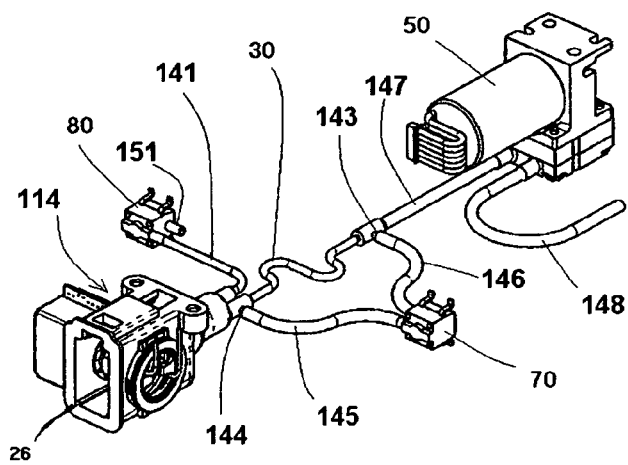
FIG. 5 is a perspective view of the sidestream gas measurement assembly and the flow monitoring/control system of the sidestream gas measurement system of FIG. 4 shown in an assembled configuration.

FIGS. 3-5 illustrate an embodiment of a sidestream gas sampling system 102, according to the principles of the present invention, that is adapted to be coupled to a multi-parameter monitoring system (not shown). Many of the features of sidestream gas sampling system 102 ancillary to the present invention are described in the '329 application, which, as noted above, is incorporated into the present invention by reference.

Sidestream gas measurement assembly 104 is contained within a housing 100 that includes a support bracket 104 and a monitor connector 106. The support bracket and monitor connector are provided for coupling housing 100 to the remaining components of the multi-parameter monitoring system, which are not illustrated herein. When housing 100 is connected to the multi-parameter monitoring system, it appears to be an integral part of the multi-parameter system or merely an extension of the housing containing the multi-parameter system. The present invention contemplates securing support bracket 104 to the remaining components of the monitor by an adhesive layer 105, as well as connector 106.

Housing 100, in the illustrated exemplary embodiment, is defined by a first housing portion 10 and a second housing portion 112 that are adapted to be joined together. Interlocking elements can be provided on housing 100 for securing the sidestream gas sampling system to the main housing of the multi-parameter system.

Sidestream gas sampling system 100 includes a gas measurement assembly, generally indicated at 114. Gas measurement assembly 114 includes sample cell receptacle 26 that receives, at least in part, the sample cell, a radiation source 118, and a radiation detector 120. When the sample cell is properly assembled with the sidestream monitor, the sample cell is seated in receptacle 26 such that radiation from source 118 passes through a sample chamber in the sample cell and is received by detector 120 after passing through the gas contained in the sample chamber. In this embodiment, receptacle 26 provides a separate, one-piece subassembly that aligns the optics of the gas sensing system and separates these optics from the rest of the components of the sidestream gas measurement assembly.

Flow generator 50 is provided in sidestream gas sampling system 100 to draw gas from the sampling site through the sample cell (gas measurement site). To dampen vibrations from the operation of the flow generator, the flow generator is placed in an isolation boot 122. A tubing system 140 connects flow generator 50, sample cell receptacle 26, valving (not shown), and an exhaust port 126. A screw 128 in conjunction with a spacer 130 and the structure of second housing portion 112 securely attaches a circuit board 132 to the second housing portion. A screw 134 attaches monitor connector 106, which interfaces to circuit board 132 via a $CO_2$ flex connector 136 to first housing portion 110.

A tubing 141 is provided at an exit of the sample cell positioned in the housing of the gas sensing system 114. Tubing 141 serves as a tap and connects to pressure sensor 80, which measures the pressure inside the sampling tube at the exit of the sample cell, i.e., the gas measurement site, relative to atmospheric pressure via port 151. The gas flow, after exiting from the sample cell, passes through a capillary tube 30. Pressure sensing lines 145 and 146 transmit the pressure at the capillary tube inlet 144 and the capillary tube outlet 143, respectively, to the input ports of the differential pressure transducer 70. After exiting the capillary tube, the gas flow passes through tubing 147 and is drawn into flow generator 50. In this embodiment, flow generator 50 is a brushless diaphragm pump. The gas flow exits the flow generator and passes through tubing 148 prior to exiting to either ambient atmosphere or a scavenging system from outlet port 126.

This method of measuring the volumetric flow Q through capillary tube 30 is based upon Poiseuille's Law, which is set forth in equation (2) below as follows:

$$Q = \left(\frac{-\pi R^4}{8\mu}\right)\frac{dP}{dz}, \tag{2}$$

where Q is volumetric flow, R is the radius of the tube, µ is the gas viscosity, and dP/dz is the axial pressure gradient (or pressure drop per unit of length of the tube).

Strictly speaking, Poiseuille's Law applies to volumetric laminar flow of an incompressible fluid, i.e., a Newtonian fluid, through a cylindrical tube with a constant circular cross-section. Whether or not the flow is laminar depends upon the Reynolds number, which is a dimensionless quantity. To achieve laminar flow, sharp transitions and obstructions within the flow path should be avoided.

As described, the laminar flow through a tube is described by Poiseuille's law, stating that the flow rate is proportional to the pressure difference between the ends of the tube and the fourth power of its radius. If the length of the tubing and its radius are known, as well as the viscosity of the fluid, then measurement of the pressure difference between the first and second portion of the tube, for example across the ends of tube, permits the flow rate to be determined.

It is important that the first portion and the second portion of the capillary tube are spaced sufficiently far apart from one another such that a measurable pressure differential exists. It is desirable that the measurable pressure differential be sufficiently large so that relatively inexpensive pressure transducers may be used. However, the use of high precision regulated pressure transducers can permit pressure differences of millitorrs to be measured.

Although viscosity of a gas is a function of temperature, it is substantially independent of pressure, i.e., gas density. Thus, the drop across a fixed length of capillary tubing will vary in proportion to flow rate, but will not vary significantly with altitude. Because the pressure gradient varies inversely with the fourth power of the radius, it is easy to get an adequate pressure drop across a relatively short length of tubing. It is to be understood, however, that the present invention contemplates using any capillary tube, regardless of diameter, length, or shape in the gas sampling system of the present invention. The method can be used to control the flow of any gas mixture in any gas sampling system requiring regulation of flow rate. The same benefits would be realized in any such application.

Because gas density is not in the equation for pressure drop in the capillary tube, altitude does not substantially affect the flow rate, contrary to conventional orifice based flow control systems. As such, the flow rate through the sampling system will remain substantially constant, regardless of the altitude at which the system is operated. Testing of the present invention conducted over the range of 350 to 750 mmHg confirm this insensitivity to changes in altitude.

The reduced sensitivity of the flow measurement to changes in gas composition can be illustrated by comparing nitrogen and helium the primary gases in air and heliox, a therapeutic gas mixture. For example, at 68 deg F. the ratio of the density and viscosity of nitrogen/helium are approximately 7 and 1.3, respectively. Therefore, capillary flow based systems are over 5 times less sensitive than orifice based systems to changes that would occur from switching from nitrogen to helium.

The capillary-based flow monitoring/control has other advantages over the traditional means that employ an orifice. One such advantage of the capillary-base flow monitoring/control system of the present invention is that it is less prone to clogging from contaminants within the sample gas path. This relates to the diameter of a typical orifice in sidestream gas measurement system, which is typically approximately 0.006 inch. The capillary tube of the present invention has an inside diameter of 0.015 inch. This 2.5× increase in diameter increases the area by more than 6× with the obvious benefit of reduced chance of clogging, thereby resulting in a more robust system. The flow regulation is independent of atmospheric pressure (altitude) and gas composition, because the viscosity of the gas determines the pressure drop generated by a capillary tube and not the gas density.

While the present invention illustrated and describe above uses a conduit type of capillary tube, it is to be understood that other embodiments for forming the capillary tube are contemplated by the present invention. For example, the capillary tube can be defined in a solid block of material. Of importance is that the characteristics of the capillary tube are provided by the capillary tube structure, and not the specific configuration for the capillary tube. In addition, the present invention describes the couplings where the pressure ports are connected to the gas flow path as T-fittings. It is to be understood that any structure that connects the pressure pick-off ports to the gas flow path are contemplated by the present invention.

Although the invention has been described in detail for the purpose of illustration based on what is currently considered to be the most practical and preferred embodiments, it is to be understood that such detail is solely for that purpose and that the invention is not limited to the disclosed embodiments, but, on the contrary, is intended to cover modifications and equivalent arrangements that are within the spirit and scope of the appended claims.

What is claimed is:

1. A sidestream gas sampling system, comprising:
   a conduit adapted to communicate a flow of gas to a gas measurement site;
   a gas measurement assembly adapted to measure a constituent of the flow of gas at the gas measurement site;
   a pressure transducer adapted to measure a pressure of the flow of gas at a first location proximate to the gas measurement site;
   a capillary tube disposed downstream of the first location and adapted to communicate the flow of gas from the gas measurement site;
   a differential pressure transducer in fluid communication with a first portion and a second portion of the capillary tube, wherein the first portion and the second portion are spaced sufficiently far apart from one another such that a pressure differential exists therebetween;
   flow generating means disposed downstream of the capillary tube for generating the flow of gas; and
   a controller operatively coupled to the pressure transducer, the differential pressure transducer, and the flow generating means, wherein the controller measures the flow of gas based on the output of the differential pressure transducer and controls the rate of flow of gas via the flow generating means based on the measured flow during operation of the flow generating means.

2. The system of claim 1, wherein the flow generating means is a pump.

3. The system of claim 1, wherein first portion is an inlet portion of the capillary tube and the second portion is an outlet portion of the capillary tube.

4. The system of claim 1, wherein the capillary tube includes at least one bend.

5. The system of claim 1, wherein the gas measurement assembly includes an emitter adapted to emit radiant energy through the gas at the gas measurement site and a detector adapted to receive the radiant energy passing through the gas at the gas measurement site.

6. The system of claim 1, wherein the controller controls the flow generating means in a feedback fashion such that the flow of gas remains constant.

7. The system of claim 1, wherein the capillary tube communicates the flow of gas from the gas measurement site to ambient atmosphere.

8. The system of claim 1, wherein the capillary tube communicates the flow of gas from the gas measurement site to the flow generating means.

9. The system of claim 1, further comprising a sample cell having an inlet operatively coupled to an end of the conduit to receive gas from the conduit and an outlet operatively coupled to the capillary tube, wherein the sample cell defines the gas measurement site.

10. The system of claim 9, wherein the sample cell is detachable from a housing containing the gas measurement assembly, the capillary tube, the flow generating means, and the controller.

11. A sidestream gas sampling system, comprising:
    gas communicating means for communicating a flow of gas to a gas measurement site;

gas measuring means for measuring a constituent of the flow of gas at the gas measurement site;

pressure sensing means for measuring a pressure of the flow of gas at a first location proximate to the gas measurement site;

flow sensing means disposed downstream of the first location for measuring the flow of gas in the gas communicating means substantially independent of a density of the flow of gas;

flow generating means for generating the flow of gas; and controlling means, operatively coupled to the pressure sensing means, the flow sensing means, and the flow generating means, for controlling the gas flow generating means based on an output of the flow sensing means.

12. The sidestream gas sampling system of claim 11, wherein the flow generating means is a pump.

13. The sidestream gas sampling system of claim 11, wherein the flow sensing means is a differential pressure transducer in fluid communication with a first portion and a second portion of a capillary tube.

14. The sidestream gas sampling system of claim 13, wherein first portion is an inlet portion of the capillary tube and the second portion is an outlet portion of the capillary tube.

15. The sidestream gas sampling system of claim 13, wherein the capillary tube includes at least one bend.

16. The sidestream gas sampling system of claim 13, wherein the capillary tube communicates the flow of gas from the gas measurement site to ambient atmosphere.

17. The sidestream gas sampling system of claim 13, wherein the capillary tube communicates the flow of gas from the gas measurement site to the flow generating means.

18. The sidestream gas sampling system of claim 13, wherein the controlling means is operatively coupled to the differential pressure transducer and the flow generating means to control the flow generating means based on an output of the differential pressure transducer.

19. The sidestream gas sampling system of claim 11, wherein the controlling means controls the flow generating means such that a rate of the flow of gas remains constant.

20. The sidestream gas sampling system of claim 11, wherein the gas measuring means includes:

radiant energy emitting means for emitting radiant energy through gas at the gas measurement site; and detecting means for receiving the radiant energy passing through the gas at the gas measurement site.

* * * * *